US011104868B2

United States Patent
Hardy et al.

(10) Patent No.: US 11,104,868 B2
(45) Date of Patent: Aug. 31, 2021

(54) LIQUID CLEANSING COMPOSITIONS WITH AN ANTIBACTERIAL SYSTEM AND METHOD OF MANUFACTURING THEREOF

(71) Applicant: Colgate-Palmolive Company, New York, NY (US)

(72) Inventors: Eugene Hardy, Old Bridge, NJ (US); Alison Kugler, Morganville, NJ (US)

(73) Assignee: Colgate-Palmolive Company, New York, NY (US)

( * ) Notice: Subject to any disclaimer, the term of this patent is extended or adjusted under 35 U.S.C. 154(b) by 34 days.

(21) Appl. No.: 16/319,855

(22) PCT Filed: Jul. 26, 2016

(86) PCT No.: PCT/US2016/044059
§ 371 (c)(1),
(2) Date: Jan. 23, 2019

(87) PCT Pub. No.: WO2018/022016
PCT Pub. Date: Feb. 1, 2018

(65) Prior Publication Data
US 2019/0270951 A1  Sep. 5, 2019

(51) Int. Cl.

| | | |
|---|---|---|
| *C11D 3/48* | (2006.01) | |
| *A61K 8/34* | (2006.01) | |
| *A61K 8/365* | (2006.01) | |
| *A61K 8/42* | (2006.01) | |
| *A61K 8/44* | (2006.01) | |
| *A61Q 17/00* | (2006.01) | |
| *A61Q 19/10* | (2006.01) | |
| *C11D 1/90* | (2006.01) | |
| *C11D 3/32* | (2006.01) | |
| *A61K 8/46* | (2006.01) | |
| *A61K 8/36* | (2006.01) | |

(52) U.S. Cl.
CPC .............. *C11D 3/48* (2013.01); *A61K 8/34* (2013.01); *A61K 8/347* (2013.01); *A61K 8/36* (2013.01); *A61K 8/365* (2013.01); *A61K 8/42* (2013.01); *A61K 8/442* (2013.01); *A61K 8/466* (2013.01); *A61Q 17/005* (2013.01); *A61Q 19/10* (2013.01); *C11D 1/90* (2013.01); *C11D 3/32* (2013.01)

(58) Field of Classification Search
None
See application file for complete search history.

(56) References Cited

U.S. PATENT DOCUMENTS

| | | |
|---|---|---|
| 5,575,652 A | 11/1996 | Gaffar et al. |
| 6,106,851 A | 8/2000 | Beerse et al. |
| 6,294,186 B1 | 9/2001 | Beerse et al. |
| 7,851,424 B2 | 12/2010 | Barnhart et al. |
| 8,329,627 B2 | 12/2012 | Gunn et al. |
| 8,501,808 B2 | 8/2013 | Dasgupta et al. |
| 8,603,550 B1 | 12/2013 | Fusco |
| 9,750,755 B2 | 9/2017 | Ahmed et al. |
| 2003/0118540 A1 | 6/2003 | Charlton et al. |
| 2004/0166084 A1* | 8/2004 | Sakai ................. A61K 8/42 424/70.27 |
| 2006/0275235 A1* | 12/2006 | Takeda ............... A61K 8/737 424/70.13 |
| 2009/0130233 A1 | 5/2009 | Kross |
| 2010/0172848 A1 | 7/2010 | Modak et al. |
| 2010/0189809 A1 | 7/2010 | Lestage et al. |
| 2010/0234328 A1 | 9/2010 | Ahmed et al. |
| 2010/0272664 A1 | 10/2010 | Subramanyam et al. |
| 2011/0268684 A1* | 11/2011 | Battermann ......... A61K 8/37 424/70.11 |
| 2014/0242198 A1* | 8/2014 | Modak ............... A01N 31/08 424/736 |

FOREIGN PATENT DOCUMENTS

| | | |
|---|---|---|
| EA | 13501 | 10/2007 |
| EP | 1630176 | 3/2006 |
| EP | 1335700 | 8/2007 |
| GB | 2431876 | 5/2007 |
| JP | 4597318 B2 * | 12/2010 |
| RU | 2517692 | 5/2014 |
| WO | 1999/058104 | 11/1999 |
| WO | 2009/073379 | 6/2009 |
| WO | 2013/066403 | 5/2013 |
| WO | 2013/067150 | 5/2013 |

OTHER PUBLICATIONS

International Search Report and Written Opinion of the International Searching Authority in International Application No. PCT/US2016/044059, dated Oct. 25, 2016.

* cited by examiner

*Primary Examiner* — Robert A Wax
*Assistant Examiner* — William Craigo

(57) ABSTRACT

A liquid cleansing composition and a method of manufacturing the same are disclosed. The liquid cleansing composition includes a cleansing component and an antibacterial system. The antibacterial system includes an antibacterial agent and an antibacterial enhancing agent. The weight ratio of the antibacterial agent to the antibacterial enhancing agent is greater than or equal to 0.30:1 and less than or equal to 0.65:1.

9 Claims, No Drawings

LIQUID CLEANSING COMPOSITIONS WITH AN ANTIBACTERIAL SYSTEM AND METHOD OF MANUFACTURING THEREOF

BACKGROUND

Conventional liquid cleansing compositions may often include antibacterial agents to reduce the transmission or risk of infection. For example, antibacterial agents are often used to disinfect surfaces in hospitals, lavatories, food prep facilities, and offices. In another example, liquid cleansing compositions, such as hand soaps and shower gels, often incorporate antibacterial agents to control the presence and growth of pathogenic microorganisms on skin to thereby reduce the transmission of disease or infection.

While conventional liquid cleansing compositions including antibacterial agents have shown efficacy in reducing the transmission of disease or infection, the incorporation of the antibacterial agents in sufficient or effective concentrations to control the pathogenic microorganisms may often produce liquid cleansing compositions having undesirable properties. For example, antibacterial agents are generally irritating to the skin when provided in the relatively high concentrations necessary to control the pathogenic microorganisms. Additionally, the antibacterial agents may often strip moisture from the skin, thereby leaving the skin feeling overly dry or chapped. Accordingly, there are competing desires to reduce the amount or concentration of the antibacterial agents while maintaining antibacterial efficacy. In addition to the foregoing, incorporating the antibacterial agents in the relatively high concentrations necessary to control the pathogenic microorganisms may be detrimental to the sensory properties or aesthetics of the liquid cleansing compositions. For example, the relatively high concentrations of the antibacterial agents may affect the foaming properties of the liquid cleansing composition, which has become publically associated with the cleaning ability of the liquid cleansing composition.

What is needed, then, are improved liquid cleansing compositions incorporating antibacterial agents having comparable or improved sensory properties.

BRIEF SUMMARY

This summary is intended merely to introduce a simplified summary of some aspects of one or more embodiments of the present disclosure. Further areas of applicability of the present invention will become apparent from the detailed description provided hereinafter. This summary is not an extensive overview, nor is it intended to identify key or critical elements of the present teachings, nor to delineate the scope of the disclosure. Rather, its purpose is merely to present one or more concepts in simplified form as a prelude to the detailed description below.

The foregoing and/or other aspects and utilities embodied in the present disclosure may be achieved by providing a liquid cleansing composition, including a cleansing component and an antibacterial system. The antibacterial system may include an antibacterial agent and an antibacterial enhancing agent. A weight ratio of the antibacterial agent to the antibacterial enhancing agent may be greater than or equal to about 0.30:1 and less than or equal to about 0.65:1.

The foregoing and/or other aspects and utilities embodied in the present disclosure may also be achieved by a method for manufacturing the liquid cleansing composition. The method for manufacturing the liquid cleansing composition may include contacting an antibacterial agent with an antibacterial enhancing agent to produce an antibacterial system. A weight ratio of the antibacterial agent to the antibacterial enhancing agent may be greater than or equal to about 0.30:1 and less than or equal to about 0.65:1. The method may also include contacting the antibacterial system with a cleansing composition to produce the liquid cleansing composition.

In another embodiment, the antibacterial enhancing agent may include an acid, and optionally, the antibacterial enhancing agent may include an organic acid.

In another embodiment, the antibacterial enhancing agent may be lactic acid.

In another embodiment, the antibacterial agent is phenoxyethanol.

In another embodiment, the weight ratio of the antibacterial agent to the antibacterial enhancing agent may be greater than or equal to about 0.35:1 and less than or equal to about 0.60:1.

In another embodiment, the weight ratio of the antibacterial agent to the antibacterial enhancing agent is greater than or equal to about 0.41:1 and less than or equal to about 0.56:1.

In another embodiment, the cleansing component may be a liquid soap, and optionally a liquid hand soap.

In another embodiment, the cleansing component may be a shower gel.

In another embodiment, the cleansing component may include one or more surfactants.

In another embodiment, the liquid cleansing composition may include at least 8.0 wt % of the one or more surfactants, and optionally at least 9.0 wt % of the one or more surfactants.

In another embodiment, the one or more surfactants may include a betaine surfactant.

In another embodiment, the betaine surfactant may be cocoamidopropyl betaine.

In another embodiment, the liquid cleansing composition may include a foam enhancer, and the foam enhancer may be cocamide monoethanolamide.

Further areas of applicability of the present invention will become apparent from the detailed description provided hereinafter. It should be understood that the detailed description and specific examples, while indicating some preferred aspects of the invention, are intended for purposes of illustration only and are not intended to limit the scope of the invention.

DETAILED DESCRIPTION

The following description of various preferred aspect(s) is merely exemplary in nature and is in no way intended to limit the invention, its application, or uses.

As used throughout, ranges are used as shorthand for describing each and every value that is within the range. Any value within the range may be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

Additionally, all numerical values are "about" or "approximately" the indicated value, and take into account experimental error and variations that would be expected by a person having ordinary skill in the art. It should be appreciated that all numerical values and ranges disclosed herein are approximate valves and ranges, whether "about" is used in conjunction therewith. It should also be appreciated that the term "about," as used herein, in conjunction with a numeral refers to a value that may be +/−1% (inclusive) of that numeral, +/−2% (inclusive) of that numeral, +/−3% (inclusive) of that numeral, +/−5% (inclusive) of that numeral, +/−10% (inclusive) of that numeral, or +/−15% (inclusive) of that numeral. It should further be appreciated that when a numerical range is disclosed herein, any numerical value falling within the range is also specifically disclosed.

Compositions

It has been surprisingly and unexpectedly discovered that an antibacterial system including an antibacterial agent (e.g., phenoxyethanol) and an antibacterial enhancing agent (e.g., an organic acid) in a weight ratio of about 0.41:1 (1:2.4) to about 0.56:1 (1:1.8) exhibits a synergistic effect that provides a significant and unexpected reduction of gram+ and gram− bacteria. It has further been surprisingly and unexpectedly discovered that a liquid cleansing composition incorporating the antibacterial system having the antibacterial agent (e.g., phenoxyethanol) and the antibacterial enhancing agent (e.g., an organic acid) in the weight ratio of about 0.41:1 (1:2.4) to about 0.56:1 (1:1.8) exhibits comparable or enhanced sensory properties. For example, it has been surprisingly and unexpectedly discovered that the liquid cleansing composition incorporating the antibacterial system exhibits enhanced or relatively greater foaming as compared to a liquid cleansing composition that does not include the antibacterial system.

The liquid cleansing composition disclosed herein may include a cleansing component and an antibacterial system. The cleansing component may be a shower gel, a liquid soap, or any other hair and/or skin cleanser. As further described herein, the antibacterial system may include one or more antibacterial agents and one or more antibacterial enhancing agents.

Antibacterial System

The antibacterial system may include one or more antibacterial agents. Illustrative antibacterial agents may include, but are not limited to, benzalkonium chloride, benzethonium chloride, 5-bromo-5-nitro-1,3-dioxane, 2-bromo-2-nitropropane-1,3-diol, alkyl trimethyl ammonium bromide, N-(hydroxymethyl)-N-(1,3-dihydroxy methyl-2,5-dioxo-4-imidaxolidinyl-N-(hydroxy methyl) urea, 1-3-dimethyol-5,5-dimethyl hydantoin, formaldehyde, iodopropynl butyl carbamate, parabens, methylisothiazolinone, mixtures of methylisothiazolinone and methylchloroisothiazoline, mixtures of phenoxyethanol/butyl paraben/methyl paraben/propylparaben, 2-phenoxyethanol, trishydroxyethyl-hexahydrotriaz-ine, methylisothiazolinone, 5-chloro-2-methyl-4-isothiazolin-3-one, 1,2-dibromo-2,4-dicyanobutane, 1-(3-chloroalkyl)-3,5,7-triaza-azoniaadamantane chloride, sodium benzoate, polyhexamethylene biguanide, alexidine, triclosan, parachlorometaxylenol, zinc pyrithione, essential oils (e.g., tea tree, eucaplyptus, thyme, etc.), silver and salts thereof, chlorhexidine and salts thereof, and the like, and combinations thereof. In a preferred embodiment, the antibacterial agent is phenoxyethanol (i.e., 2-phenoxyethanol).

The antibacterial system may also include one or more antibacterial enhancing agents configured to increase or enhance the activity of the antibacterial agent. The antibacterial enhancing agent may be or include one or more acids, such as organic acids. Illustrative organic acids may include, but are not limited to, citric acid, acetic acid, lactic acid, glycolic acid, formic acid, butyric acid, propionic acid, valeric acid, malic acid, oxalic acid, carbonic acid, taurine, and the like, and combinations thereof. In a preferred embodiment, the antibacterial enhancing agent is lactic acid.

In at least one embodiment, a weight ratio of the antibacterial agent to the antibacterial enhancing agent may be greater than or equal to about 0.30:1 and less than or equal to about 0.60:1. For example, the weight ratio of the antibacterial agent to the antibacterial enhancing agent may be about 0.30:1, about 0.35:1, about 0.40:1, or about 0.45:1 to about 0.50:1, about 0.55:1, or about 0.60:1. In a preferred embodiment, the weight ratio of the antibacterial agent to the antibacterial enhancing agent may be from about 0.41:1 to about 0.56:1 (about 1:1.8 to about 1:2.4). In another example, the weight ratio of the antibacterial agent to the antibacterial enhancing agent may be about 0.30:1 to about 0.60:1, about 0.35:1 to about 0.55:1, about 0.40:1 to about 0.50:1, about 0.42:1 to about 0.48:1, or about 0.44:1 to about 0.46:1. In another embodiment, the weight ratio of the antibacterial agent to the antibacterial enhancing agent may be greater than or equal to about 0.65:1 and less than or equal to about 1:1. For example, the weight ratio of the antibacterial agent to the antibacterial enhancing agent may be about 0.65:1, about 0.70:1, about 0.75:1, or about 0.80:1 to about 0.85:1, about 0.90:1, about 0.95:1, or about 1:1. In another example, the weight ratio of the antibacterial agent to the antibacterial enhancing agent may be about 0.65:1 to about 1:1, about 0.70:1 to about 0.95:1, about 0.75:1 to about 0.90:1, or about 0.80:1 to about 0.85:1.

Surfactants

The liquid cleansing composition may include one or more surfactants. In at least one embodiment, the surfactants may be or include a salt of a $C_{10-16}$ alcohol ethoxylate sulfate, a betaine surfactant, and/or an alkyl polyglucoside. In another embodiment, the liquid cleansing composition may include one or more anionic surfactants, one or more cationic surfactants, one or more zwitterionic surfactants, one or more nonionic surfactants, and mixtures thereof. The amount of the surfactants in the liquid cleansing composition may be from about 5.0 wt % to about 14.0 wt %. For example, the amount of the surfactants in the liquid cleansing composition may be from about 5.0 wt %, about 6.0 wt %, about 7.0 wt %, about 8.0 wt % or about 9.0 wt % to about 10.0 wt %, about 11.0 wt %, about 12.0 wt %, about 13.0 wt %, or about 14.0 wt %. In another embodiment, the amount of the surfactants in the liquid cleansing composition may be from about 8.0 wt % to about 15.0 wt %. For example, the amount of the surfactants in the liquid cleansing composition may be from about 8.0 wt %, about 9.0 wt %, about 10.0 wt %, or about 11.0 wt % to about 12.0 wt %, about 13.0 wt %, about 14.0 wt %, or about 15.0 wt %. In another example, the amount of the surfactants in the liquid cleansing composition may be about 8.0 wt % to about 15.0 wt %, about 9.0 wt % to about 14.0 wt %, about 10.0 wt % to about 13.0 wt %, or about 11.0 wt % to about 12.0 wt %.

The salt of the $C_{10-16}$ alcohol ethoxylate sulfate may be any one or more salts of the $C_{10-16}$ alcohol ethoxylate sulfate. In at least one example, the $C_{10-16}$ may be lauryl. The average moles of ethylene oxide may be from 1 to 30. In a preferred embodiment, the average moles of the ethylene oxide is 1 to 3. The cation of the salt may be any suitable cation of the $C_{10-16}$ alcohol ethoxylate sulfate. For example, the cation may be an alkali metal (e.g., sodium, potassium, etc.), an alkaline earth metal (e.g., calcium), ammonium, triethanolamine, and the like. In an exemplary embodiment, the salt of the $C_{10-16}$ alcohol ethoxylate sulfate is sodium lauryl ether sulfate. The sodium lauryl ether sulfate may have an average of 2 moles of the ethylene oxide.

As previously discussed, the one or more surfactants may include a betaine surfactant. Illustrative betaine surfactants may include, but are not limited to, cocodimethylcarboxymethyl betaine, cocamidopropyl betaine, lauryldimethylcarboxymethyl betaine, lauryldimethylcarboxyethyl betaine, cetyldimethylcarboxymethyl betaine, lauryl-bis-(2-hydroxyethyl)carboxymethyl betaine, oleyldimethylgammacarboxypropyl betaine, and lauryl-bis-(2-hydroxypropyl)-carboxyethyl betaine, and the like, and combinations thereof. In a preferred embodiment, the betaine surfactant is a cocamidopropyl betaine. The alkyl polyglucoside may include any suitable alkyl group. For example, the alkyl group may be a decyl, a lauryl, or a coco. In a preferred embodiment, the alkyl polyglucoside is decyl glucoside.

In an exemplary embodiment, the surfactants of the liquid cleansing composition may include 60-70 weight % of the salt of a $C_{10-16}$ alcohol ethoxylate sulfate, 20-30 wt % betaine surfactant, and 5-15 wt % alkyl polyglucoside, based on a total weight of the surfactants. In another embodiment, the surfactants of the liquid cleansing composition may include 66 to 67 wt %, or about 66.4 wt % of the salt of a $C_{10-16}$ alcohol ethoxylate sulfate, 24 to 25 wt %, or about 24.4 wt % of the betaine surfactant, and 9 to 10 wt %, or about 9.2 wt % of the alkyl polyglucoside.

In at least one embodiment, the liquid cleansing composition may include at least one anionic surfactant. Illustrative anionic surfactants may include, but are not limited to, water-soluble salts of higher fatty acid monoglyceride monosulfates, such as a sodium salt of a monosulfated monoglyceride of hydrogenated coconut oil fatty acids, such as sodium N-methyl N-cocoyl taurate, sodium cocomonoglyceride sulfate. Illustrative anionic surfactants may also include higher alkyl sulfates. As used herein, "higher alkyl" refers to $C_{6-30}$ alkyl. For example, the anionic surfactant may be or include sodium lauryl sulfate. The anionic surfactants may also include higher alkyl-ether sulfates. In another embodiment, the anionic surfactant may include higher alkyl aryl sulfonates, such as sodium dodecyl benzene sulfonate (sodium lauryl benzene sulfonate), and higher alkyl sulfoacetates, such as sodium lauryl sulfoacetate (dodecyl sodium sulfoacetate), higher fatty acid esters of 1, 2 dihydroxy propane sulfonate, sulfocolaurate (N-2-ethyl laurate potassium sulfoacetamide) and sodium lauryl sarcosinate. In an exemplary embodiment, the anionic surfactant may be or include a water soluble salt of alkyl sulfates having from 10 to 18 carbon atoms in the alkyl radical and water soluble salts of sulfonated monoglycerides of fatty acids having from 10 to 18 carbon atoms. For example, the anionic surfactant may be or include, sodium lauryl sulfate, sodium lauroyl sarcosinate, sodium coconut monoglyceride sulfonates, or the like, and mixtures thereof.

In at least one embodiment, the liquid cleansing composition may include at least one nonionic surfactant. The nonionic surfactant may function as an emulsifier. Illustrative nonionic surfactants may include, but are not limited to, poloxamers and the like. For example, the nonionic surfactants may include polysorbate 20, poloxamer 407, poloxamer 338, poloxamer 124, and the like, and mixtures thereof. The nonionic surfactants may also include, but are not limited to, ethoxylated and hydrogenated ethoxylated castor oils, such as those commonly designated as PEG NN castor oil or PEG NN hydrogenated castor oil, where "NN" designates the number of ethylene oxide units polymerized onto the castor oil to form the nonionic surfactant. For example, the nonionic surfactants may be or include PEG 16, 20, 25, 30, 40, 50, 60, 80, 100, 200, and combinations thereof. In a preferred embodiment, the nonionic surfactant is PEG 40 hydrogenated castor oil, which is commercially available as CREMOPHOR® RH40 from BASF Corp. of Florham Park, N.J.

Fatty Alcohol

The liquid cleansing composition may include one or more fatty alcohols. The fatty alcohols may be or include a $C_{12-18}$ fatty alcohol, or preferably a $C_{16-18}$ fatty alcohol. Illustrative fatty alcohols may include, but are not limited to, lauryl alcohol, myristyl alcohol, cetyl alcohol and stearyl alcohol. The amount of the fatty alcohols in the liquid cleansing composition may be greater than or equal to 8 wt % and less than or equal to 25 wt %.

Carrier

The carrier of the liquid cleansing composition may be or include water. Water of the liquid cleansing composition may be deionized water, demineralized water, and/or softened water. In an exemplary embodiment, the carrier of the liquid cleansing composition includes demineralized water and softened water. Water may make up the balance of the liquid cleansing composition. For example, the amount of water in the liquid cleansing composition may be from about 10 wt % to 90 wt %, about 40 wt % to about 85 wt %, or about 60 wt % to about 80 wt %. In another example, the amount of water in the liquid cleansing composition may be at least 60 wt %, at least 65 wt %, at least 70 wt %, at least 72 wt %, at least 74 wt %, at least 76 wt %, at least 78 wt %, or at least 79 wt %. In at least one embodiment, the amount of demineralized water may be about 50 wt %, about 51 wt %, about 52 wt %, about 53 wt %, about 54 wt %, or about 55 wt %, and the amount of softened water may be about 18 wt %, about 19 wt %, about 20 wt %, about 21 wt %, or about 22 wt %. The amount of water in the liquid cleansing composition may include free water added and water introduced with other components or materials of the liquid cleansing composition. For example, the amount of the water in the liquid cleansing composition may include free water and water associated with the surfactants or any other component of the liquid cleansing composition.

Skin Care Agents

In some embodiment, the liquid cleansing composition may include one or more skin care agents. Any suitable skin care agents that do not adversely affect the stability and/or efficacy of the liquid cleansing composition may be used. In at least one embodiment, the skin care agent may include an emollient configured to maintain a soft, smooth, and pliable appearance to the skin. As is known by those skilled in the art, the emollients may function by remaining on the surface of the skin or in the stratum corneum to act as a lubricant, to reduce flaking, and/or to improve the appearance of the skin.

The skin care agents may generally include one or more polymers (e.g., polyvinylpyrrolidine), protein derivatives (e.g., derivatized hydrolyzed wheat protein), ethoxylated fatty ethers, cellulosics (e.g., hydroxyethylcellulose), and the like, and combinations thereof. Illustrative skin care agents may include, but are not limited to, esters comprising an aliphatic alcohol having about 2 to about 18 carbon atoms condensed with an aliphatic or aromatic carboxylic acid including about 8 to about 20 carbon atoms (e.g., isopropyl myristate, decyl oleate, cetearyl isononanate, etc.). The esters may be straight chained or branched. In a preferred embodiment, the ester has a molecular weight of less than about 500.

Other skin care agents may include, but are not limited to, polyvinyl-pyrrolidone, polyquaternium-4, polyquaternium-7, polyquaternium-10, guar gum derivatives, hydroxypropylmethylcellulose, hydroxyethylcellulose, a polyethylene glycol, a methyl ether of a polyethylene glycol, quaternium-79, wheat germamidopropyl hydroxypropyl dimonium hydrolyzed wheat protein, stearyl methicone, dimethicone copolyol, dimethicone propyl PG betaine, poly(sodium styrene sulfonate), sorbitan oleate, steareth-2, steareth-21, isoceteth-20, PEG-7 glyceryl cocoate, PEG-75 lanolin, glycereth-26, PPG-5-ceteth-20, a $C_{12}$-$C_{20}$ alcohol, canola oil, glyceryl laurate, triglyceryl monostearate, glyceryl monostearate, vitamin E acetate, sunflower seed amidopropylethyldimonium ethylsulfate, sodium PEG-7 olive oil carboxylate, PPG-1 hydroxyethyl caprylamide, PPG-2 hydroxyethyl cocamide, mineral oil, petrolatum, aloe barbadensis, isostearamidopropylmorpholine lactate, strontium acetate, palmitamidopropyltrimonium chloride, and the like, and combinations thereof. In a preferred embodiment, the skin care agent is or includes a conditioner, such as a cationic cellulose polymer (e.g., polyquaternium-7).

Additional Optional Components/Ingredients

The liquid cleansing composition may include one or more additional optional ingredients. Illustrative optional ingredients may include, but are not limited to, one or more dyes, fragrances, buffers and buffering agents (e.g., inorganic phosphates, sulfates, and carbonates), pH adjusters (e.g., acids and/or bases), preservatives (e.g., parabens, sodium salicylate, sodium benzoate, etc.), thickeners, viscosity modifiers, antioxidants, foam enhancers, chelating agents (e.g., EDTA, phosphates, etc.), opacifiers, hydric solvents, hydrotropes, humectants, antimicrobials, and the like, and combinations thereof.

Illustrative basic pH adjusters may include ammonia; mono-, di-, and tri-alkyl amines; mono-, di-, and tri-alkanolamines; alkali metal and alkaline earth metal hydroxides; and the like, and combinations thereof. For example, the basic pH adjuster may be ammonia, sodium hydroxide, potassium hydroxide, lithium hydroxide, monoethanolamine, triethylamine, isopropanolamine, diethanolamine, triethanolamine, and the like, and combinations thereof.

Illustrative acidic pH adjusters may include mineral acids and polycarboxylic acids. The mineral acids may be or include hydrochloric acid, nitric acid, phosphoric acid, sulfuric acid, and the like, and combinations thereof. The polycarboxylic acids may be or include citric acid, glycolic acid, lactic acid, and the like, and combinations thereof.

The liquid cleansing composition may have a neutral pH, an alkaline pH, or an acidic pH. In a preferred embodiment, the liquid cleansing composition is at least partially acidic. For example, the liquid cleansing composition may have a pH less than 7. In another example, the liquid cleansing composition may have a pH greater than or equal to 1 and less than 7. For example, the liquid cleansing composition may have a pH of about 1, about 2, about 3, or about 4 to about 5, about 6, or about 6.9. In another example, the liquid cleansing composition may have a pH from about 1 to less than 7, about 2 to about 6, or about 3 to about 5. In a preferred embodiment, the liquid cleansing composition has a pH from about 3.6 to about 4.2.

The foam enhancer may be or include, but is not limited to, cocamide MEA (i.e., cocamide monoethanolamide), cocamide DEA, soyamide DEA, lauramide DEA, oleamide MIPA, stearamide MEA, myristamide MEA, lauramide MEA, capramide DEA, ricinoleamide DEA, myristamide DEA, stearamide DEA, oleylamide DEA, tallowamide DEA, lauramide MIPA, tallowamide MEA, isostearamide DEA, isostearamide MEA, and the like, and combinations thereof. In a preferred embodiment, the foam enhancer is cocamide MEA.

Illustrative humectants may include, but are not limited to, ascorbic acid, ascorbyl dipalmitate, acetamide MEA, glucose glutamate, glucuronic acid, TEA-lactate, TEA-PCA, corn syrup, fructose, glucose, glycerin, glycol, 1,2,6-hexanetriol, sodium lactate, sodium PCA, hydrogenated starch hydrolysate, inositol, lactic acid, lactose, mannitol, PCA, PEG-10 propylene glycol, polyamino sugar condensate, propylene glycol, pyridoxine dilaurate, saccharide hydrolysate, hydroxystearyl methylglucamine, glucamine, maltitol, mannitol, methyl gluceth-10, methyl gluceth-20, riboflavin, PEG-4, PEG-6, PEG-8, PEG-9, PEG-10, PEG-12, PEG-14, PEG-16, PEG-18, PEG-20, PEG-32, PEG-40, glutamic acid, glycereth-7, glycereth-12, glycereth-26, saccharide isomerate, sorbeth-20, sorbitol, sucrose, thioglycerin, tris-(hydroxymethyl)nitromethane, tromethamine, histidine, PEG-75, PEG-135, PEG-150, PEG-200, PEG-5 pentaerythritol ether, polyglyceryl sorbitol, sorbitol, urea, xylitol, and the like, and combinations thereof.

Methods

In one or more embodiments, the present disclosure provides methods for cleansing skin and controlling the presence and/or growth of bacteria on the skin including contacting the skin with the liquid cleansing composition disclosed herein. The present disclosure may also provide methods for producing, fabricating, or otherwise manufacturing the liquid cleansing composition. The present disclosure may also provide methods for providing the liquid cleansing composition that maintains or improves one or more sensory properties (e.g., foaming) of the liquid cleansing composition.

EXAMPLES

The following examples and other embodiments described herein are exemplary and not intended to be limiting in describing the full scope of compositions and methods of this disclosure. Equivalent changes, modifications and variations of specific embodiments, materials, compositions and methods may be made within the scope of the present disclosure, with substantially similar results.

Example 1

A series of liquid cleansing compositions (1)-(9) were prepared by combining the ingredients/components according to Table 1. Each of the liquid cleansing compositions (1)-(9) included varying amounts of the antibacterial agent, phenoxyethanol, and varying amounts of the antibacterial enhancing agent, lactic acid.

TABLE 1

Composition of Liquid Cleansing Compositions (1)-(9)

| Ingredients/Components | 1 | 2 | 3 | 4 | 5 | 6 | 7 | 8 | 9 |
|---|---|---|---|---|---|---|---|---|---|
| Deionized Water | QS | QS | QS | QS | QS | QS | QS | QS | QS |
| Surfactants | 9.53 | 9.53 | 9.53 | 11.89 | 13.23 | 13.47 | 13.47 | 9.53 | 9.53 |
| Phenoxyethanol (PE) | 0.74 | 0.90 | 0.90 | 0.74 | — | 0.90 | 0.90 | 0.90 | — |
| Lactic Acid (LA) | 1.80 | 1.80 | 0.25 | 1.80 | 1.80 | 0.25 | — | — | 1.00 |
| Fragrance | 0.55 | 0.45 | 0.55 | 1.10 | 0.45 | 0.45 | 0.45 | 0.55 | 0.55 |
| pH Adjuster | QS | QS | QS | QS | QS | QS | QS | QS | QS |
| Chelating Agent | 0.11 | 0.11 | 0.11 | 0.11 | 0.11 | 0.11 | 0.11 | 0.11 | 0.11 |
| Sodium Benzoate | 0.32 | 0.32 | 0.32 | 0.32 | 0.32 | 0.32 | 0.32 | 0.32 | 0.32 |
| Sodium Salicylate | 0.23 | 0.23 | 0.23 | 0.23 | 0.23 | 0.23 | 0.23 | 0.23 | 0.23 |
| Glycerin | 0.15 | 0.15 | 0.15 | 0.15 | 0.0 | 0.0 | 0.0 | 0.15 | 0.15 |
| Dye | 0.00175 | 0.00175 | 0.00175 | 0.00175 | 0.00175 | 0.00175 | 0.00175 | 0.00175 | 0.00175 |

To validate the antibacterial system for use in pharmaceutical, medical, dental, veterinary, agri-food, and industrial sectors, and for domestic or community use, an in-vitro antibacterial efficacy study was performed on each of the liquid cleansing compositions (1)-(9). For the in-vitro antibacterial efficacy study, each of the liquid cleansing compositions (1)-(9) was evaluated in accordance with the procedures of the European Standard (NF EN 1040: Chemical Disinfectants And Antiseptics—Quantitative Suspension Test For The Evaluation Of Basic Bactericidal Activity Of Chemical Disinfectants And Antiseptics). According to the European Standard (NF EN 1040), a disinfecting agent (e.g., the antibacterial system) must kill 99.999% of the targeted bacteria (i.e., a 5-log reduction) using an inoculum of $10^8$ cfu/ml of the gram+ and gram− bacteria (i.e., *E. coli* and *S. Aureus*). The results of the in-vitro antibacterial efficacy study are summarized in Table 2.

Panel of eight expert panelists for sensory properties via a blind sequential monadic block design. Each of the eight expert panelists assessed each of the liquid cleansing compositions (4) and (5) using a standardized methodology and a 0-15 point assessment scale, where '0' represented the lowest value (i.e., none or low) and '15' represented the highest value. Each of the liquid cleansing compositions (4) and (5) were blinded and coded with a random three-digit number. The order of sample presentation was balanced and randomize across all the panelists. The panelists evaluated each of the liquid cleansing compositions (4) and (5) for a range of sensory properties or characteristics including: product attributes before and during washing, lather attributes on pouf and hands during washing, skin feel attributes on hands and forearms during rinsing and after drying. The results of the Expert Sensory Panel are summarized in Table 3.

TABLE 2

In-Vitro Antibacterial Efficacy Results

| | 1 | 2 | 3 | 4 | 5 | 6 | 7 | 8 | 9 |
|---|---|---|---|---|---|---|---|---|---|
| PE (wt %) | 0.74 | 0.90 | 0.90 | 0.74 | — | 0.90 | 0.90 | 0.90 | — |
| LA (wt %) | 1.80 | 1.80 | 0.25 | 1.80 | — | 0.25 | — | — | 1.00 |
| Ratio of PE:LA | 0.41:1 | 0.50:1 | 3.6:1 | 0.41:1 | — | 3.6 | — | — | — |
| *E. coli* (Log Reduction) | 7.24 | 7.37 | 0.48 | 7.34 | 3.21 | 2.66 | 2.67 | 0.32 | 0.37 |
| *S. aureus* (Log Reduction) | 7.10 | 7.87 | 5.02 | 7.28 | 7.87 | 5.81 | 5.43 | 5.87 | 4.88 |

As is evident from Table 2, including the phenoxyethanol (PE) alone, as in liquid cleansing compositions (7) and (8), or the lactic acid (LA) alone, as in liquid cleansing compositions (5) and (9), did not achieve the 5-log reduction of the gram+ and gram− bacteria. As such, the liquid cleansing compositions (5) and (7)-(9) did not pass the European Standard (NF EN 1040). As further evident from Table 2, including the phenoxyethanol and the lactic acid outside the preferred ratio of from about 0.41:1 to about 0.56:1 (about 1:1.8 to about 1:2.4), as in liquid cleansing compositions (3) and (6) also did not achieve the 5-log reduction of the gram+ and gram− bacteria. However, the liquid cleansing compositions (1), (2), and (4) including both the antibacterial agent (e.g., phenoxyethanol) and the antibacterial enhancing agent (e.g., lactic acid) in the preferred ratio exhibited a reduction of the gram+ and gram− bacteria in an amount greater than the minimum 5-log.

Example 2

The liquid cleansing compositions (4) and (5) from Example 1 were further evaluated by an Expert Sensory

TABLE 3

Expert Sensory Panel Results of Liquid Cleansing Compositions (4) and (5)

| Sensory Property | 4 | 5 |
|---|---|---|
| LATHER ATTRIBUTES DURING WASHING: | | |
| Amount of Foam-5T | 3.7 | 3.4 |
| Amount of Foam-10T | 8.3 | 8.4 |
| Amount of Foam-20T | 14.2 | 14.0 |
| Bubble Size-10T | 3.2 | 3.3 |
| Bubble Size-20T | 2.0 | 2.0 |
| Density of Foam-10T | 8.1 | 8.1 |
| Density of Foam-20T | 12.1 | 12.0 |
| Peaking-10T | 1.0 | 1.0 |
| Peaking-20T | 1.8 | 2.1 |
| Firmness-10T | 2.0 | 2.0 |
| Firmness-20T | 4.0 | 4.0 |
| On Hands: | | |
| Amount of Foam-5R | 1.7 | 1.6 |
| Amount of Foam-10R | 2.6* | 1.5 |

TABLE 3-continued

Expert Sensory Panel Results of Liquid Cleansing Compositions (4) and (5)

| Sensory Property | 4 | 5 |
|---|---|---|
| Amount of Foam-20R | 5.9 | 5.4 |
| Amount of Creamy Foam-5R | 0.0 | 0.2 |
| Amount of Creamy Foam-10R | 1.3 | 2.2 |
| Amount of Creamy Foam-20R | 0.0 | 0.5 |
| PRODUCT FEEL DURING WASHING: | | |
| Ease of Spread | 11.7 | 11.6 |
| Slimy | 5.2 | 5.5 |
| Creamy | 5.3 | 5.7 |
| Thickness | 6.4 | 6.3 |
| SKIN FEEL DURING RINSING: | | |
| Slip-5L | 12.2 | 11.8 |
| Slip-10L | 11.0 | 10.8 |
| Slip-15L | 10.1 | 10.3 |
| Slip-Arm removed from water | 10.0 | 10.1 |
| SKIN FEEL AFTER DRYING: | | |
| Slip-immediate | 6.4 | 6.4 |
| Slip-2M | 8.2 | 8.0 |
| Slip-5M | 8.2 | 8.2 |
| Stickiness-Immediate | 0.3 | 0.0 |
| Tautness-Immediate | 0.0 | 0.0 |
| Tautness-2M | 0.0 | 0.0 |
| Tautness-5M | 0.0 | 0.0 |
| Moistness-2M | 8.3 | 8.3 |
| Moistness-5M | 9.0 | 8.8 |
| Fragrance Intensity-5M | 5.3 | 4.8 |
| Fragrance Intensity-15M | 3.6 | 3.5 |

*Statistically significant at 90% Confidence Level

The liquid cleansing composition (4) of Example 1, which exhibited a greater than minimum 5-log reduction of bacteria, was found to provide similar sensory properties in each category as compared to the liquid cleansing composition (5), which did not exhibit a greater than minimum 5-log reduction of bacteria. Additionally, the liquid cleansing composition (4) exhibited statistically significant increase in foaming lather (Amount of Foam-10R) as compared to the liquid cleansing composition (5).

Accordingly, it has been surprisingly and unexpectedly discovered that the antibacterial system including phenoxyethanol and the antibacterial enhancing agent (e.g., lactic acid) in a weight ratio of about 0.41:1 to about 0.56:1 (about 1:1.8 to about 1:2.4) exhibits a synergistic effect that provides a significant and unexpected reduction of gram+ and gram− bacteria. It has further been surprisingly and unexpectedly discovered that the liquid cleansing composition disclosed herein including the antibacterial system exhibits comparable or enhanced sensory properties (e.g., foaming).

The present disclosure has been described with reference to exemplary embodiments. Although a limited number of embodiments have been shown and described, it will be appreciated by those skilled in the art that changes may be made in these embodiments without departing from the principles and spirit of the preceding detailed description. It is intended that the present disclosure be construed as including all such modifications and alterations insofar as they come within the scope of the appended claims or the equivalents thereof.

What is claimed is:

1. A liquid cleansing composition, comprising:
    a cleansing component; and
    an antibacterial system, the antibacterial system comprising:
        an antibacterial agent; and
        an antibacterial enhancing agent,
    wherein a weight ratio of the antibacterial agent to the antibacterial enhancing agent is greater than or equal to about 0.41:1 and less than or equal to about 0.56:1;
    wherein the antibacterial agent is phenoxyethanol present in an amount of from 0.74 wt % to 0.90 wt %, and
    wherein the antibacterial enhancing agent is lactic acid present in an amount of about 1.8 wt %.

2. The liquid cleansing composition according to claim 1, wherein the cleansing component is a liquid soap, and optionally a liquid hand soap.

3. The liquid cleansing composition according to claim 1, wherein the cleansing component is a shower gel.

4. The liquid cleansing composition according to claim 1, wherein the cleansing component comprises one or more surfactants.

5. The liquid cleansing composition according to claim 4, wherein the liquid cleansing composition comprises at least 8.0 wt % of the one or more surfactants, and optionally at least 9.0 wt % of the one or more surfactants.

6. The liquid cleansing composition according to claim 4, wherein the one or more surfactants comprise a betaine surfactant.

7. The liquid cleansing composition of claim 6, wherein the betaine surfactant is cocoamidopropyl betaine.

8. The liquid cleansing composition according to claim 1, further comprising a foam enhancer, wherein the foam enhancer is cocamide monoethanolamide.

9. A method for manufacturing the liquid cleansing composition of claim 1, comprising:
    contacting an antibacterial agent with an antibacterial enhancing agent to produce an antibacterial system; and
    contacting the antibacterial system with a cleansing composition to produce the liquid cleansing composition;
    wherein a weight ratio of the antibacterial agent to the antibacterial enhancing agent is greater than or equal to about 0.41:1 and less than or equal to about 0.56:1;
    wherein the antibacterial agent is phenoxyethanol present in an amount of from 0.74 wt % to 0.90 wt %, and
    wherein the antibacterial enhancing agent is lactic acid present in an amount of about 1.8 wt %.

* * * * *